(12) United States Patent
Suelmann

(10) Patent No.: US 10,716,272 B2
(45) Date of Patent: Jul. 21, 2020

(54) CUCUMBER VARIETY NUN 51024 CUP

(71) Applicant: Nunhems B.V., Nunhem (NL)

(72) Inventor: Johannes Josephus Suelmann, Roermond (NL)

(73) Assignee: NUNHEMS B.V., Nunhem (NL)

( * ) Notice: Subject to any disclaimer, the term of this patent is extended or adjusted under 35 U.S.C. 154(b) by 0 days.

(21) Appl. No.: 16/047,685

(22) Filed: Jul. 27, 2018

(65) Prior Publication Data

US 2018/0368350 A1    Dec. 27, 2018

Related U.S. Application Data

(60) Provisional application No. 62/541,170, filed on Aug. 4, 2017.

(51) Int. Cl.
| | | |
|---|---|---|
| *A01H 5/08* | (2018.01) | |
| *A01H 6/34* | (2018.01) | |
| *A01H 5/10* | (2018.01) | |
| *A01H 4/00* | (2006.01) | |
| *A01H 1/08* | (2006.01) | |
| *A01H 1/04* | (2006.01) | |

(52) U.S. Cl.
CPC ............... *A01H 5/10* (2013.01); *A01H 1/04* (2013.01); *A01H 1/08* (2013.01); *A01H 4/008* (2013.01); *A01H 5/08* (2013.01); *A01H 6/346* (2018.05)

(58) Field of Classification Search
None
See application file for complete search history.

(56) References Cited

U.S. PATENT DOCUMENTS

| | | |
|---|---|---|
| 4,822,949 A | 4/1989 | Niego et al. |
| 5,349,128 A | 9/1994 | Quemada et al. |
| 5,492,827 A | 2/1996 | Dirks |
| 6,084,152 A | 7/2000 | Kwak et al. |
| 6,765,130 B2 | 7/2004 | Taurick |

FOREIGN PATENT DOCUMENTS

| | | |
|---|---|---|
| WO | WO 2014/076249 A1 | 5/2014 |
| WO | WO 2016/120438 A1 | 8/2016 |
| WO | WO 2016/207432 A1 | 12/2016 |

OTHER PUBLICATIONS

Colijn-Hooymans, J.C., et al., "Competence for regeneration of cucumber cotyledons is restricted to specific developmental stages", Plant Cell, Tissue and Organ Culture, 1994, vol. 39, pp. 211-217.

Needleman, S.B., et. al., "A general method applicable to the search for similarities in the amino acid sequence of two proteins", Journal of Molecular Biology, 1970, vol. 48, pp. 443-453.

Parvathaneni, R. K., et. al., "Fingerprinting in Cucumber and Melon (*Cucumis* spp.) Genotypes using morphological and ISSR markers", Journal of Crop Science and Biotechnology, 2011, vol. 14(1), pp. 39-43.

Pisanu, A. B., et al., "Yield and Biometric Characteristics of 9 Clones Selected from the Population of "Spinoso sardo" Artichokes", Acta Hort., 2004, ISHS 660.

Rice, P., et, al, "EMBOSS: The European Molecular Biology Open Software Suite", Trends in Genetics, 2000, vol. 16, No. 6 pp. 276-277.

Sang-Gu, K., et al., Callus growth and plant regeneration in diverse cultivars of cucumber (*Cucumis sativus* L.), Plant Cell, Tissue and Organ Culture, 1988, vol. 12, pp. 67-74.

Sarreb, D. A., et al., "Comparison of triploid and diploid cucumber in long-term liquid cultures," Plant Cell, Tissue and Organ Culture, 2002, vol. 71, issue 3, pp. 231-235.

UPOV, "Guidelines for the Conduct of Tests for Distinctness, Uniformity and Stability," TG/61/7 (Geneva 2007, last revised 2016).

USDA, "Objective Description of Variety—Cucumber (*Cucumis sativus* L.)", https://www.ams.usda.gov/sites/default/files/media/93-Cucumber%20ST-470-93%202015.pdf.

Nikotova, V., et. al., "Diploidization of cucumber (*Cucumis sativus* L.) Haploids by Colchicine Treatment", Acta Societatis Botanicorum Poloniae, 1996, vol. 65, No. 3-4, pp. 311-317.

Vidaysky, F., et. al., "Tomato Breeding Lines Resistant and Tolerant to Tomato Yellow Leaf Curl Virus Issued from Lycopersicon hirsutum", The American Phytopathology Society, 1998, vol. 88, No. 9, pp. 910-914.

Vos, P., et al., "AFLP: a new technique for DNA fingerprinting", Nucleic Acid Research, 1995, vol. 23, No. 21, pp. 4407-4414.

Wijnker, E., et al., "Hybrid recreation by reverse breeding in *Arabidopsis thaliana*", Nature Protocols, 2014, vol. 9, No. 4, pp. 761-772.

*Primary Examiner* — Brent T Page
(74) *Attorney, Agent, or Firm* — Arent Fox LLP

(57) ABSTRACT

The disclosure provides a new and distinct hybrid variety of cucumber, NUN 51024 CUP as well as seeds and plants and fruits thereof.

27 Claims, No Drawings

CUCUMBER VARIETY NUN 51024 CUP

CROSS-REFERENCE TO RELATED APPLICATIONS

The application claims the benefit of U.S. Patent Application Ser. No. 62/541,170, filed Aug. 4, 2017, which is incorporated herein by reference in its entirety.

FIELD OF THE INVENTION

The disclosure relates to the field of plant breeding and, more specifically, to cucumber variety NUN 51024 CUP. The disclosure further relates to vegetative reproductions NUN 51024 CUP, methods for tissue culture of NUN 51024 CUP and regenerating a plant from such a tissue culture, and to phenotypic variants of NUN 51024 CUP.

BACKGROUND

The goal of plant breeding is to combine various desirable traits in a single variety/hybrid. Such desirable traits may include greater yield, resistance to diseases, insects or other pests, tolerance to heat and drought, better agronomic quality, higher nutritional value, enhanced growth rate and improved fruit properties.

Breeding techniques take advantage of a plant's method of pollination. There are two general methods of pollination: a plant self-pollinates if pollen from one flower is transferred to the same or another flower of the same genotype. A plant cross-pollinates if pollen comes to it from a flower of a different genotype.

Plants that have been self-pollinated and selected for (uniform) type over many generations become homozygous at almost all gene loci and produce a uniform population of true breeding progeny of homozygous plants. A cross between two such homozygous plants of different lines produces a uniform population of hybrid plants that are heterozygous for many gene loci. The extent of heterozygosity in the hybrid is a function of the genetic distance between the parents. Conversely, a cross of two plants each heterozygous at a number of loci produces a segregating population of hybrid plants that differ genetically and are not uniform. The resulting non-uniformity makes performance unpredictable.

The development of uniform varieties requires the development of homozygous inbred plants, the crossing of these inbred plants to make hybrids, and the evaluation of the hybrids resulting from the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new plants are evaluated to determine which have commercial potential.

Cucumber (*Cucumis sativus* L.) is naturally a diploid (2n=14) outcrossing species, although haploid, doubled-haploid (see, e.g., U.S. Pat. No. 5,492,827 hereby incorporated by reference in its entirety), and triploid (see, e.g., Sarreb et al. (2002), Plant Cell Tissue, Organ Culture 71: 231-235) types have been developed. The two main types of cucumber fruit grown commercially today in the United States are fresh market (slicing) type and the processing (pickling) type. Varieties and production methods are typically adapted to the end use. Slicing cucumbers are often longer, larger and have darker and thicker skin, whereas pickling/processing cucumbers have a shorter fruit, thinner skin with interior flesh that make them more amenable to pickling. Seedless varieties are generally preferable for both fresh market and for pickling as seeds are not palatable.

Cucumber plants that set fruit parthenocarpically (without pollination and fertilization) have more recently been available. These plants produce seedless fruit unless pollinated. Growth of parthenocarpic varieties is beneficial in that setting of fruit on these cultivars does not produce an inhibiting effect on plant growth, unlike the case of fertilized, seeded fruit. The seedless varieties are usually higher yielding and of higher quality due to the lack of seeds. However, growth of these plants requires isolation from seeded cucumbers to avoid pollination and subsequent seeded fruit.

Most of the cucumbers currently grown for processing to pickles and pickle products in the United States are seeded hybrid varieties. Hybrid varieties offer the advantages of easy combination of dominant and recessive traits, such as disease resistance, from a set of inbred parents, as well as careful control of parentage. The production of F1 hybrid cucumber seeds from a pollen parent bearing only male flowers has been reported (see, e.g., U.S. Pat. No. 4,822,949).

Many different cucumber cultivars have been produced, and cucumber breeding efforts have been underway in many parts of the world (see e.g., U.S. Pat. No. 6,765,130). Some breeding objectives include varying the color, texture and flavor of the fruit. Minimizing the occurrence of bitterness in cucumbers is one such example. Other objectives include optimizing flesh thickness, solid content (% dry matter), and sugar content. Also, breeding programs have focused on developing plants with earlier fruit maturity; more restricted vine growth, improved disease resistance or tolerance, and improved adaptability to environmental conditions.

Advances in biotechnology have also resulted in genetically engineered cucumber plants with improved traits. For example, cucumbers resistant to CMV have been developed by expression of CMV protein coat genes (see e.g., U.S. Pat. No. 5,349,128). Transgenic plants exhibiting, for example, other viral resistance traits or high levels of superoxide dismutase have also been reported (see e.g., U.S. Pat. No. 6,084,152).

While breeding efforts to date have provided a number of useful cucumber varieties with beneficial traits, there remains a great need in the art for new varieties with further improved traits. Such plants would benefit farmers and consumers alike by improving crop yields and/or quality. Some breeding objectives include varying the color, texture and flavor of the fruit, and absence of seeds. Other objectives include disease or pest resistance, optimizing flesh thickness, yield, suitability to various climatic circumstances, solid content (% dry matter), and storage properties.

SUMMARY OF VARIOUS EMBODIMENTS OF THE INVENTION

The disclosure provides for cucumber variety NUN 51024 CUP, products thereof, and methods of using the same. NUN 51024 CUP is a pickling cucumber and is suitable for processing by pickling in a brine, vinegar, marinade or other solutions.

In one aspect, the disclosure provides a seed of cucumber variety NUN 51024 CUP, wherein a representative sample of said seed has been deposited under Accession Number NCIMB 43122. The disclosure also provides for a plurality of seeds of NUN 51024 CUP. The cucumber seed of NUN 51024 CUP may be provided as an essentially homogeneous population of cucumber seed. The population of seed of NUN 51024 CUP may be particularly defined as essentially free from other seed. The seed population may be grown into plants to provide an essentially homogeneous population of cucumber plants as described herein.

The disclosure also provides a plant grown from a seed of cucumber variety NUN 51024 CUP and a plant part thereof. In another aspect, the disclosure provides for a hybrid variety of NUN 51024 CUP. The disclosure also provides for a progeny of variety NUN 51024 CUP. In another aspect, the disclosure provides a plant or a progeny retaining all or all but one, two or three of the "distinguishing characteristics" or all or all but one, two or three of the "morphological and physiological characteristics" of variety NUN 51024 CUP and methods for producing that plant or progeny.

In one aspect, the disclosure provides a plant or a progeny having all the physiological and morphological characteristics of variety NUN 51024 CUP when grown under the same environmental conditions. In another aspect, the plant or progeny has all or all but one, two or three of the physiological and morphological characteristics of NUN 51024 CUP when measured under the same environmental conditions and evaluated at significance levels of 1%, 5% or 10% significance (which can also be expressed as a p-value), wherein a representative sample of seed of variety NUN 51024 CUP has been deposited under Accession Number NCIMB 43122. In another aspect, the plant or progeny has all or all but one, two or three of the physiological and morphological characteristics as listed in Table 1 for variety NUN 51024 CUP when measured under the same environmental conditions and evaluated at significance levels of 1%, 5% or 10% significance (which can also be expressed as a p-value).

In another aspect, a plant of NUN 51024 CUP or a progeny thereof has 4, 5, 6, 7, 8, or more, or all of the following distinguishing characteristics: 1) cotyledon bitterness; 2) plant growth type; 3) plant total length of first 15 internodes; 4) leaf blade ratio length of terminal lobe/length of blade; 5) time of development of female flowers; 6) plant number of female flowers per node; 7) fruit diameter; 8) fruit creasing; 9) fruit degree of creasing; 10) fruit density of vestiture; 11) fruit length of stripes; and 12) fruit length of peduncle.

In other aspects, the disclosure provides for a plant part obtained from variety NUN 51024 CUP, wherein said plant part is: a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said variety, hypocotyl, cotyledon, a scion, a stock, a rootstock, a pistil, an anther, or a flower or a part thereof. Fruits are particularly important plant parts. In another aspect, the plant part obtained from variety NUN 51024 CUP is a cell, optionally a cell in a cell or tissue culture. That cell may be grown into a plant of NUN 51024 CUP.

The disclosure also provides a cell culture of NUN 51024 CUP and a plant regenerated from NUN 51024 CUP, which plant has all the characteristics of NUN 51024 CUP when grown under the same environmental conditions, as well as methods for regenerating NUN 51024 CUP. Alternatively, a regenerated plant may have one characteristic that is different from NUN 51024 CUP.

The disclosure further provides a vegetatively propagated plant of variety NUN 51024 CUP having all or all but one, two or three of the morphological and physiological characteristics of NUN 51024 CUP when grown under the same environmental conditions.

The disclosure furthermore provides a cucumber fruit produced on a plant grown from a seed of NUN 51024 CUP.

In another aspect, the disclosure provides a seed growing or grown on a plant of NUN 51024 CUP (i.e., produced after pollination of the flower of NUN 51024 CUP).

Definitions

"Cucumber" refers herein to plants of the species *Cucumis sativus*. The most commonly eaten part of a cucumber is the fruit or pepo. The fruit comprises a stem and peduncle or pedicel, receptacle, ectocarp, rind, fruit flesh, exocarp, mesocarp, external phloem, internal phloem, xylem, vascular bundle, carpel, placenta and optionally seed. The stem and peduncle or pedicel, receptacle, ectocarp, rind, fruit flesh, exocarp, mesocarp, external phloem, internal phloem, xylem, vascular bundle, carpel, placenta and seed coat of the seed are maternal tissues, and are genetically identical to the plant on which they grow.

"Cultivated cucumber" refers to plants of *Cucumis sativus* (e.g., varieties, breeding lines or cultivars of the species *C. sativus*), cultivated by humans and having good agronomic characteristics.

"Pickling cucumber" refers to cucumbers suitable for processing by pickling in a brine, vinegar, marinade or other solution. Said processing includes allowing the cucumbers to ferment for a period of time by immersion in an acidic liquid or though lacto-fermentation. Pickled pickling cucumbers are also known as pickles or gherkins.

The terms "cucumber plant designated NUN 51024 CUP", "NUN 51024 CUP", "NUN 51024", "NUN 51024 F1", "51024 CUP" or "cucumber 51024" are used interchangeably herein and refer to a cucumber plant of variety NUN 51024 CUP, representative seed of which having been deposited under Accession Number NCIMB 43122.

A "seed of NUN 51024 CUP" refers to a cucumber seed which can be grown into a plant of NUN 51024 CUP, wherein a representative sample of viable seed of NUN 51024 CUP has been deposited under Accession Number NCIMB 43122. A seed can be in any stage of maturity, for example, a mature, viable seed, or an immature, non-viable seed. A seed comprises an embryo and maternal tissues.

An "embryo of NUN 51024 CUP" refers to an "F1 hybrid embryo" as present in a seed of NUN 51024 CUP, a representative sample of said seed of NUN 51024 CUP having been deposited under Accession Number NCIMB 43122.

A "seed grown on NUN 51024 CUP" refers to a seed grown on a mature plant of NUN 51024 CUP or inside a fruit of NUN 51024 CUP. The "seed grown on NUN 51024 CUP" contains tissues and DNA of the maternal parent, NUN 51024 CUP. The "seed grown on NUN 51024 CUP" contains an F2 embryo. When said seed is planted, it grows into a first generation progeny plant of NUN 51024 CUP.

A "fruit of NUN 51024 CUP" refers to a fruit containing maternal tissues of NUN 51024 CUP as deposited under Accession Number NCIMB 43122. In one aspect, the fruit contains seed grown on NUN 51024 CUP. In another aspect, the fruit does not contain seed, i.e., the fruit is parthenocarpic. The skilled person is familiar with methods for inducing parthenocarpy. Those methods comprise chemically or genetically inducing parthenocarpy. Compounds suitable for chemically inducing parthenocarpy include auxins, gibberellins and cytokinins. Genetic parthenocarpy can be induced (see e.g., WO2016207432 and WO2016120438 (PIN4) which are herein incorporated by reference in their entirety) or can be provided by reduced or eliminated expression of PISTILATA (PI) or APETALA3 (AP3). A fruit can be in any stage of maturity, for example, a mature fruit in the yellow stage comprising viable seed, or an immature fruit in the edible green stage comprising non-viable seed.

An "essentially homogeneous population of cucumber seed" is a population of seeds where at least 97%, 98%, 99% or more of the total population of seed are seed of NUN 51024 CUP.

An "essentially homogeneous population of cucumber plants" is a population of plants where at least 97%, 98%, 99% or more of the total population of plants are plants of NUN 51024 CUP.

The phrase "essentially free from other seed" refers to a population of seed where less than 3%, 2%, 1% or less of the total population of seed is seed that is not a cucumber seed or, in another aspect, less than 3%, 2%, 1% or less of the total population of seed is seed that is not seed of NUN 51024 CUP.

"Tissue culture" or "cell culture" refers to a composition comprising isolated cells of the same or a different type or a collection of such cells organized into parts of a plant. Tissue culture of various tissues of cucumber and regeneration of plants therefrom is well known and widely published (see, e.g., Sang-Gu et al. (1988), Plant Cell, Tissue and Organ Culture 12: 67-74; Colijn-Hooymans (1994), Plant Cell, Tissue and Organ Culture 39: 211-217). Similarly, methods of preparing cell cultures are known in the art.

"UPOV descriptors" are the plant variety descriptors described for cucumber in the "Guidelines for the Conduct of Tests for Distinctness, Uniformity and Stability, TG/61/7 (Geneva 2007, last revised 2016), as published by UPOV (International Union for the Protection of New Varieties and Plants, available on the world wide web at upov.int) and which can be downloaded from the world wide web at upov.int/under edocs/tgdocs/en/tg061.pdf and is herein incorporated by reference in its entirety.

"USDA descriptors" are the plant variety descriptors for cucumber as described in the document titled "OBJECTIVE DESCRIPTION OF VARIETY—Cucumber (*Cucumis sativus* L.)" as published by the US Department of Agriculture, Agricultural Marketing Service, Plant Variety Protection Office, Beltsville, Md. 20705 and which can be downloaded from the World Wide Web at ams.usda.gov/under sites/default/files/media/93-Cucumber.pdf. "Non-USDA descriptors" are other descriptors suitable for describing cucumber.

"RHS" refers to the Royal Horticultural Society of England which publishes an official botanical color chart quantitatively identifying colors according to a defined numbering system. The chart may be purchased from Royal Horticulture Society Enterprise Ltd RHS Garden; Wisley, Woking; Surrey GU236QB, UK, e.g., the RHS color chart: 2007 (The Royal Horticultural Society, charity No: 222879, PO Box 313 London SW1P2PE.

"Plant part" includes any part of a plant, such as a plant organ (e.g., harvested or non-harvested fruits), a plant cell, a plant protoplast, a plant cell tissue culture or a tissue culture from which a whole plant can be regenerated, a plant cell that is intact in a plant, a clone, a micropropagation, plant callus, a plant cell clump, a plant transplant, a vegetative propagation, a seedling, a fruit, a harvested fruit, a part of a fruit, a leaf, a part of a leaf, pollen, an ovule, an embryo, a petiole, a shoot or a part thereof, a stem or a part thereof, a root or a part thereof, a root tip, a cutting, a seed, a part of a seed, hypocotyl, cotyledon, a scion, a graft, a stock, a rootstock, a pistil, an anther, and a flower or parts of any of these and the like. Seed can be mature or immature. Pollen or ovules may be viable or non-viable. Also any developmental stage is included, such as seedlings, cuttings prior or after rooting, mature plants or leaves. Alternatively, a plant part may also include a plant seed which comprises maternal tissues of NUN 51024 CUP and an embryo having one or two sets of chromosomes derived from the parent plant, e.g., from NUN 51024 CUP. Such an embryo comprises two sets of chromosomes derived from NUN 51024 CUP if it is produced from self-pollination of NUN 51024 CUP, while an embryo derived from cross-fertilization of NUN 51024 CUP will comprise only one set of chromosomes from NUN 51024 CUP.

"Harvested plant material" refers herein to plant parts (e.g., fruits detached from the whole plant), which have been collected for further storage and/or further use.

"Reference Variety" refers herein to variety Justina, a commercial variety from Nunhems B.V., which has been planted in a trial together with NUN 51024 CUP. In one aspect, characteristics of NUN 51024 CUP may be compared to the USDA descriptors of Justina.

"Rootstock" or "stock" refers to the plant selected for its roots, in particular for the resistance of the roots to diseases or stress (e.g., heat, cold, salinity etc.). Normally, the quality of the fruit of the plant providing the rootstock is less important.

"Scion" refers to a part of the plant attached to the rootstock. This plant is selected for its stems, leaves, flowers, or fruits. The scion contains the desired genes to be duplicated in future production by the stock/scion plant and may produce the desired cucumber fruit.

"Stock/scion" or "grafted plant" refers to a cucumber plant comprising a rootstock from one plant grafted to a scion from another plant.

A plant having "all the physiological and morphological characteristics" of a referred-to-plant means a plant showing the physiological and morphological characteristics of the referred-to-plant when grown under the same environmental conditions, preferably in the same experiment; the referred-to-plant can be a plant from which it was derived, e.g., the progenitor plant, the parent, the recurrent parent, the plant used for tissue- or cell culture, etc. A physiological or morphological characteristic can be a numerical characteristic or a non-numerical characteristic. In one aspect, a plant has "all but one, two or three of the physiological and morphological characteristics" of a referred-to-plant, or "all the physiological and morphological characteristics" of Table 1 or "all or all but one, two or three of the physiological and morphological characteristics" of Table 1.

The physiological and/or morphological characteristics mentioned above are commonly evaluated at significance levels of 1%, 5% or 10% if they are numerical, or for having an identical degree (or type) if not numerical, if measured under the same environmental conditions. For example, a progeny plant or a Single Locus Converted plant or a mutated plant of NUN 51024 CUP may have one or more (or all) of the essential physiological and/or morphological characteristics of said variety listed in Table 1, as determined at the 5% significance level (i.e., $p<0.05$), when grown under the same environmental conditions.

"Distinguishing characteristics" or "distinguishing morphological and/or physiological characteristics" refers herein to the characteristics which distinguish the new variety from other cucumber varieties, such as the Reference Variety (i.e., are different), when grown under the same environmental conditions. The distinguishing characteristics between NUN 51024 CUP and Reference Variety are described herein and also can be seen in Table 1. When comparing NUN 51024 CUP to other varieties, the distinguishing characteristics may be different. In one aspect, the distinguishing characteristics may include one, two, three or more (or all) of the characteristics listed in Table 1. Preferably, all numerical distinguishing characteristics are statistically significantly different at p<0.05 between NUN 51024 CUP and the other variety (e.g., the Reference Variety).

NUN 51024 CUP has the following distinguishing characteristics when compared to the Reference Variety: 1) cotyledon bitterness; 2) plant growth type; 3) plant total length of first 15 internodes; 4) leaf blade ratio length of terminal lobe/length of blade; 5) time of development of female flowers; 6) plant number of female flowers per node; 7) fruit diameter; 8) fruit creasing; 9) fruit degree of creasing; 10) fruit density of vestiture; 11) fruit length of stripes; and 12) fruit length of peduncle. This can be seen in Table 1, where characteristics of NUN 51024 CUP are compared to the characteristics of the Reference Variety, when grown under the same environmental conditions Thus, a cucumber plant "comprising the distinguishing characteristics of NUN 51024 CUP" (such as a progeny plant) refers herein to a plant which does not differ significantly from said variety in the distinguishing characteristics above. Therefore, in one aspect, a plant is provided which does not differ significantly from NUN 51024 CUP in the distinguishing characteristics above.

Similarity and differences between two different plant lines or varieties can be determined by comparing the number of morphological and/or physiological characteristics that are the same (i.e., statistically not significantly different) or that are different (i.e., statistically significantly different) between the two plant lines or varieties using plants grown under the same environmental conditions. Preferably, a numerical characteristic is considered to be "the same" when the value for a numeric characteristic is not significantly different at the 1% (p<0.01) or 5% (p<0.05) significance level, using one way analysis of variance (ANOVA), a standard method known to the skilled person. Preferably, non-numerical or "degree" or "type" characteristic are considered "the same" when the values have the same "degree" or "type" when scored using USDA and/or UPOV descriptors, if the plants are grown under the same environmental conditions.

A "plant line" is, for example, a breeding line which can be used to develop one or more varieties. A breeding line is typically highly homozygous.

"Hybrid variety" or "F1 hybrid" refers to the seeds harvested from crossing two inbred (nearly homozygous) parental lines. For example, the female parent is pollinated with pollen of the male parent to produce hybrid (F1) seeds on the female parent.

"Regeneration" refers to the development of a plant from cell culture or tissue culture or vegetative propagation.

"Vegetative propagation", "vegetative reproduction" or "clonal propagation" are used interchangeably herein and mean a method of taking a plant part and inducing or allowing that plant part to form at least roots, and also refer to the plant or plantlet obtained by that method. Optionally, the vegetative propagation is grown into a mature plant. The skilled person is aware of what plant parts are suitable for use in the method.

"Crossing" refers to the mating of two parent plants. The term encompasses "cross-pollination" and "selfing".

"Selfing" refers to self-pollination of a plant, i.e., the transfer of pollen from the anther to the stigma of the same plant.

"Cross-pollination" refers to the fertilization by the union of two gametes from different plants.

"Yield" means the total weight of all cucumber fruits harvested per hectare of a particular line or variety. It is understood that "yield" expressed as weight of all cucumber fruits harvested per hectare can be obtained by multiplying the number of plants per hectare times the "yield per plant". "Marketable yield" means the total weight of all marketable cucumber fruits, especially fruit which is not cracked, damaged or diseased, harvested per hectare of a particular line or variety. A "marketable fruit" is a fruit that has commercial value.

As used herein, the terms "resistance" and "tolerance" are used interchangeably to describe plants that show no symptoms or significantly reduced symptoms to a specified biotic pest, pathogen, abiotic influence or environmental condition compared to a susceptible plant. These terms are optionally also used to describe plants showing some symptoms but that are still able to produce marketable product with an acceptable yield.

"Harvest maturity" is referred to as the stage at which a cucumber fruit is ripe or ready for harvest or the optimal time to harvest the fruit for the market, for processing or for consumption. In one aspect, harvest maturity is the stage which allows proper completion of the normal ripening.

"Flavor" refers to the sensory impression of a food or other substance, especially a cucumber fruit or fruit part (fruit flesh) and is determined mainly by the chemical senses of taste and smell. Flavor is influenced by texture properties and by volatile and/or non-volatile chemical components (organic acids, lipids, carbohydrates, salts etc.).

"Aroma" refers to smell (or odor) characteristics of cucumber fruits or fruit parts (fruit flesh).

The term "traditional breeding techniques" encompasses herein crossing, selfing, selection, doubled haploid production, embryo rescue, protoplast fusion, marker assisted selection, mutation breeding etc. as known to the breeder (i.e., methods other than genetic modification/transformation/transgenic methods), by which, for example, a genetically heritable trait can be transferred from one cucumber line or variety to another. It optionally includes epigenetic modifications.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce a progeny plant. Progeny plants which have the trait are then crossed to the recurrent parent. After several generations of backcrossing and/or selfing the recurrent parent comprises the trait of the donor. The plant generated in this way may be referred to as a "single trait converted plant". The technique can also be used on a parental line of a hybrid.

"Progeny" as used herein refers to a plant obtained from a plant designated NUN 51024 CUP. A progeny may be obtained by regeneration of cell culture or tissue culture or parts of a plant of said variety or selfing of a plant of said variety or by producing seeds of a plant of said variety. In further aspects, progeny may also encompass plants obtained from crossing of at least one plant of said variety with another cucumber plant of the same variety or another variety or line, or with wild cucumber plants. A progeny may comprise a mutation or a transgene. A "first generation progeny" is the progeny directly derived from, obtained from, obtainable from or derivable from the parent plant by, e.g., traditional breeding methods (selfing and/or cross-pollinating) or regeneration (optionally combined with transformation or mutation). Thus, a plant of NUN 51024 CUP is the male parent, the female parent or both of a first generation progeny of NUN 51024 CUP. Progeny may have all the physiological and morphological characteristics of NUN 51024 CUP when grown under the same environmental conditions. Using methods such as backcrossing, recurrent selection, mutation or transformation, one or more specific characteristics may be introduced into said variety, to provide or a plant comprising all but 1, 2, or 3 of the morphological and physiological characteristics of NUN 51024 CUP.

The terms "gene converted" or "conversion plant" or "single locus converted plant" in this context refer to cucumber plants which are developed by backcrossing wherein essentially all of the desired morphological and physiological characteristics of the parent variety or line are recovered, in addition to the one or more genes transferred into the parent via the backcrossing technique (optionally including reverse breeding or reverse synthesis of breeding lines) or via genetic engineering or through mutation breeding. Likewise, a "Single Locus Converted (Conversion) Plant" refers to plants developed by plant breeding techniques comprising or consisting of mutation and/or by genetic transformation and/or by backcrossing, wherein essentially all of the desired morphological and physiological characteristics of a cucumber variety are recovered in addition to the characteristics of the single locus having been transferred into the variety via the backcrossing technique. In case of a hybrid, the gene may be introduced in the male or female parental line.

"Marker" refers to a readily detectable phenotype, preferably inherited in codominant fashion (both alleles at a locus in a diploid heterozygote are readily detectable), with no environmental variance component, i.e., a heritability of 1.

"Average" refers herein to the arithmetic mean.

The term "mean" refers to the arithmetic mean of several measurements. The skilled person understands that the appearance of a plant depends to some extent on the growing conditions of said plant. Thus, the skilled person will know suitable growing conditions for NUN 51024 CUP. The mean, if not indicated otherwise within this application, refers to the arithmetic mean of measurements on at least 10 different, randomly selected plants of a variety or line.

DETAILED DESCRIPTION OF VARIOUS EMBODIMENTS OF THE INVENTION

The disclosure relates to a plant of NUN 51024 CUP, wherein a representative sample of seeds of said variety was deposited under the Budapest Treaty, with Accession number NCIMB 43122.

The disclosure also relates to a seed of cucumber variety, referred to as NUN 51024 CUP, wherein a representative sample of said seed was deposited under the Budapest Treaty, with Accession number NCIMB 43122.

In another aspect, the disclosure provides for a cucumber plant part of variety NUN 51024 CUP, preferably a fruit, a representative sample of seed from said variety has been deposited under the Budapest Treaty, with Accession number NCIMB 43122.

A seed of hybrid variety NUN 51024 CUP is obtainable by crossing the male parent of NUN 51024 CUP with the female parent of NUN 51024 CUP, and harvesting the seeds produced on the female parent. The resultant seeds of said variety can be grown to produce plants of said variety. In one aspect, a seed or a plurality of seeds of said variety are packaged into a container of any size or type (e.g., bags, cartons, cans, etc.). The seed may be disinfected, primed and/or treated with various compounds, such as seed coatings or crop protection compounds. The seed produces a plant of NUN 51024 CUP.

Also provided is a plant of NUN 51024 CUP, or a fruit or other plant part thereof, produced from a seed, wherein a representative sample of said seeds has been deposited under the Budapest Treaty, with Accession Number NCIMB 43122.

Also provided is a plant part obtained from variety NUN 51024 CUP, wherein said plant part is a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on NUN 51024 CUP, hypocotyl, cotyledon, a scion, a stock, a rootstock, a pistil, an anther, and a flower or a part thereof. Fruits are particularly important plant parts. Fruits may be parthenocarpic, or seedless, or contain immature or nonviable seeds, or contain viable seeds. In a further aspect, the plant part obtained from variety NUN 51024 CUP is a cell, optionally a cell in a cell or tissue culture. That cell may be grown into a plant of NUN 51024 CUP. A part of NUN 51024 CUP (or of a progeny of that variety or of a plant having all physiological and/or morphological characteristics but one, two or three of NUN 51024 CUP) further encompasses any cells, tissues, organs obtainable from the seedlings or plants in any stage of maturity.

The disclosure also provides for a food or feed product or a processed product comprising or consisting of a plant part described herein. Preferably, the plant part is a cucumber fruit or part thereof and/or an extract from a fruit or another plant part described herein comprising at least one cell of NUN 51024 CUP. The food or feed product may be fresh or processed, e.g., dried, grinded, powdered, pickled, chopped, cooked, roasted, in a sauce, in a sandwich, pasted, puréed or concentrated, juiced, pickled, canned, steamed, boiled, fried, blanched and/or frozen, etc.

Such a plant part of NUN 51024 CUP can be stored and/or processed further. The disclosure thus also provides for a food or feed product comprising one or more of such parts, such as canned, chopped, cooked, roasted, in a sauce, in a sandwich, pasted, puréed or concentrated, juiced, frozen, dried, pickled, or powdered cucumber fruit from NUN 51024 CUP or from progeny of said variety, or from a derived variety, such as a plant having all but one, two or three physiological and/or morphological characteristics of NUN 51024 CUP.

In another aspect, the disclosure provides for a cucumber fruit of variety NUN 51024 CUP, or a part of a fruit of said variety. The fruit can be in any stage of maturity, for example, immature or mature. In another embodiment, the disclosure provides for a container comprising or consisting of a plurality of harvested cucumber fruits or parts of fruits of said variety, or fruits of progeny thereof, or fruits of a derived variety.

Marketable fruits are generally sorted by size and quality after harvest. Alternatively, the fruits can be sorted by expected shelf life, pH or Brix.

In another aspect, the plant, plant part or seed of NUN 51024 CUP is inside one or more containers, such as cans, boxes, crates, bags, cartons, Modified Atmosphere Packaging, films (e.g., biodegradable films), etc. comprising a plant or a plant part or a seed (fresh and/or processed) of NUN 51024 CUP. In a particular aspect, the container comprises a plurality of seeds of NUN 51024 CUP, or a plurality of plant parts of NUN 51024 CUP.

The disclosure further relates to a cucumber variety, referred to as NUN 51024 CUP, which—when compared to its REFERENCE VARIETY Justina—has the following distinguishing characteristics: 1) cotyledon bitterness; 2) plant growth type; 3) plant total length of first 15 internodes; 4) leaf blade ratio length of terminal lobe/length of blade; 5) time of development of female flowers; 6) plant number of female flowers per node; 7) fruit diameter; 8) fruit creasing; 9) fruit degree of creasing; 10) fruit density of vestiture; 11) fruit length of stripes; and 12) fruit length of peduncle, where the characteristics are determined at the 5% significance level for plants grown under the same environmental conditions. Also encompassed are parts of that plant.

In another aspect, NUN 51024 CUP has resistance to *Cladosporium cucumerinum* that is 9 (1 susceptible/9 resistant) measured according to UPOV standards. In another aspect, NUN 51024 CUP has resistance to Cucumber Mosaic Virus (CMV) that is 2 (1 susceptible/2 moderately resistant/3 highly resistant) measured according to UPOV standards. In another aspect, NUN 51024 CUP has resistance to powdery mildew (*Podosphaera xanthii*) that is 3 (1 susceptible/2 moderately resistant/3 highly resistant) measured according to UPOV standards. In another aspect, NUN 51024 CUP has resistance to *Cladosporium cucumerinum*, Cucumber Mosaic Virus and powdery mildew as described herein. The UPOV standards for measuring resistance to *Cladosporium cucumerinum*, Cucumber Mosaic Virus, and powdery mildew (*Podosphaera xanthii*) can be found on world wide web at upov.int/ under edocs/tgdocs/en/tg061.pdf, which is herein incorporated by reference in its entirety.

The disclosure further provides a cucumber plant which does not differ from the physiological and morphological characteristics of the plant of NUN 51024 CUP as determined at the 1%, 2%, 3%, 4% or 5% significance level when grown under the same environmental conditions. In a particular aspect, the plants are measured in the same trial (e.g., the trial is conducted as recommended by the USDA or UPOV). The disclosure also comprises a part of said plant.

The disclosure also provides a tissue or cell culture comprising cells of NUN 51024 CUP. Such a tissue culture can, for example, be grown on plates or in liquid culture, or be frozen for long term storage. The cells of NUN 51024 CUP used to start the culture can be selected from any plant part suitable for vegetative reproduction, or, in a particular aspect, can be cells of an embryo, meristem, a cotyledon, a hypocotyl, pollen, a leaf, an anther, a root, a root tip, a pistil, a petiole, a flower, a fruit, seed or a stem. In another particular aspect, the tissue culture does not contain somaclonal variation or has reduced somaclonal variation. The skilled person is familiar with methods to reduce or prevent somaclonal variation, including regular re-initiation.

In one aspect, the disclosure provides a cucumber plant regenerated from the tissue or cell culture of NUN 51024 CUP, wherein the regenerated plant is not significantly different from NUN 51024 CUP in all, or all but one, two or three, of the physiological and morphological characteristics (determined at the 5% significance level when grown under the same environmental conditions). Optionally, the plant has one, two or three the physiological and morphological characteristics that are affected by a mutation or by transformation. In another aspect, the disclosure provides a cucumber plant regenerated from the tissue or cell culture of NUN 51024 CUP, wherein the plant has all of the physiological and morphological characteristics of said variety determined at the 5% significance level when grown under the same environmental conditions. Similarity or difference of a characteristic is determined by measuring that characteristics on a representative number of plants grown under the same environmental conditions, determining whether type/degree characteristics are the same and determining whether numerical characteristics are different at the 5% significance level.

NUN 51024 CUP, or its progeny, or a plant having all physiological and/or morphological characteristics but one, two or three which are different from those of NUN 51024 CUP, can also be reproduced using vegetative reproduction methods. Therefore, the disclosure provides for a method of producing a plant, or a plant part, of NUN 51024 CUP, comprising vegetative propagation of said variety. Vegetative propagation comprises regenerating a whole plant from a plant part of NUN 51024 CUP or from a progeny or from or a plant having all physiological and/or morphological characteristics of said variety but one, two or three different characteristics, such as a cutting, a cell culture or a tissue culture.

The disclosure also provides methods of vegetatively propagating a part of the plant of the disclosure NUN 51024 CUP. In certain aspects, the method comprises: (a) cultivating tissue or cells capable of being propagated from NUN 51024 CUP to obtain proliferated shoots; and (b) rooting said proliferated shoots, to obtain rooted plantlets. Steps (a) and (b) may also be reversed, i.e., first cultivating said tissue to obtain roots and then cultivating the tissue to obtain shoots, thereby obtaining rooted plantlets. The rooted plantlets may then be further grown, to obtain plants. In one embodiment, the method further comprises step (c) growing plants from said rooted plantlets. Therefore, the method also comprises regenerating a whole plant from a part of NUN 51024 CUP. In a particular aspect, the part of the plant to be propagated is a cutting, a cell culture or a tissue culture.

The disclosure also provides for a vegetatively propagated plant of variety NUN 51024 CUP (or from progeny of NUN 51024 CUP or from or a plant having all but one, two or three physiological and/or morphological characteristics of NUN 51024 CUP), wherein the plant has all of the morphological and physiological characteristics of NUN 51024 CUP when the characteristics are determined at the 5% significance level for plants grown under the same conditions. In another aspect, the propagated plant has all but one, two or three of the morphological and physiological characteristics of NUN 51024 CUP when the characteristics are determined at the 5% significance level for plants grown under the same conditions. A part of said propagated plant or said propagated plant with one, two or three differences is also included.

In another aspect, the disclosure provides a method for producing a plant part, preferably a fruit, comprising growing a plant of NUN 51024 CUP until it sets at least one fruit, and collecting the fruit. Preferably, the fruit is collected at harvest maturity. In another embodiment, the fruit is collected when the seed is ripe. In a particular aspect, all fruits on a truss can be harvested together. In another particular aspect, all fruit on a plant can be harvested at the same time. A plant of NUN 51024 CUP can be produced by seeding directly in the soil (e.g., the field) or by germinating the seeds in a controlled environment (e.g., a greenhouse) and optionally then transplanting the seedlings into the field. For example, a seed is sown into a prepared seed bed in a field where the plant remains for its entire life. Alternatively, the cucumber seed may be planted through a black plastic mulch. The dark plastic will absorb heat from the sun, warming the soil early. It will also help to conserve moisture during the growing season, controls weeds and makes harvesting easier and cleaner. A plant of NUN 51024 CUP can also be grown entirely in greenhouses.

In still another aspect, the disclosure provides a method of producing a cucumber plant, comprising crossing a plant of NUN 51024 CUP with a second cucumber plant at least once, allowing seed to develop and optionally harvesting said progeny seed. The skilled person can select progeny from said crossing. Optionally, the progeny (grown from the progeny seed) is crossed twice, thrice, or four, five, six or seven times, and allowed to set seed. In one aspect, the first "crossing" further comprises planting seeds of a first and a second parent cucumber plant, often in proximity so that pollination will occur; for example, mediated by insect vectors. Alternatively, pollen can be transferred manually. Where the plant is self-pollinated, pollination may occur without the need for direct human intervention other than plant cultivation. After pollination the plant can produce seed.

The disclosure also provides a method for developing a plant in a breeding program, using NUN 51024 CUP, or its parts as a source of plant breeding material. Suitable plant breeding techniques are recurrent selection, backcrossing, pedigree breeding, mass selection, mutation breeding and/or genetic marker enhanced selection. In one aspect, the method comprises crossing NUN 51024 CUP or its progeny, or a plant comprising all but 1, 2, or 3 or more of the morphological and physiological characteristics of NUN 51024 CUP (e.g., as listed in Table 1), with a different plant, and wherein one or more offspring of the crossing are subject to one or more plant breeding techniques: recurrent selection, backcrossing, pedigree breeding, mass selection, mutation breeding and genetic marker enhanced selection (see e.g., Vidaysky and Czosnek, (1998) Phytopathology 88(9): 910-4). For breeding methods in general see Principles of Plant Genetics and Breeding, 2007, George Acquaah, Blackwell Publishing, ISBN-13: 978-1-4051-3646-4.

In yet another aspect, the disclosure provides a method of producing a plant, comprising selfing a plant of variety NUN 51024 CUP one or more times, and selecting a progeny plant from said selfing. In one aspect, the progeny plant retains all or all but one, two or three of the physiological and morphological characteristic of NUN 51024 CUP described above when grown under the same environmental conditions. In a different aspect, the progeny plant comprises all of the physiological and morphological characteristic of NUN 51024 CUP of Table 1.

In other aspects, the disclosure provides a progeny plant of variety NUN 51024 CUP such as a progeny plant obtained by further breeding of NUN 51024 CUP. Further breeding with NUN 51024 CUP includes selfing that variety and/or cross-pollinating NUN 51024 CUP with another cucumber plant one or more times. In particular, the disclosure provides for a progeny plant that retains all the morphological and physiological characteristics of NUN 51024 CUP or, in another aspect, a progeny plant that retains all, or all but one, two or three, of the morphological and physiological characteristics of NUN 51024 CUP, optionally all or all but one, two or three of the characteristics as listed in Table 1, determined at the 5% significance level for numerical characteristics, when grown under the same environmental conditions. In another aspect, the progeny is a first generation progeny, i.e., the ovule or the pollen (or both) used in the crossing is an ovule or pollen of NUN 51024 CUP, where the pollen comes from an anther of NUN 51024 CUP and the ovule comes from an ovary of NUN 51024 CUP. In another aspect, the disclosure provides for a vegetative reproduction of the variety and a plant having all, or all but 1, 2, or 3 of the physiological and morphological characteristics of NUN 51024 CUP (e.g., as listed in Table 1).

The disclosure also provides a method for collecting pollen of NUN 51024 CUP, comprising collecting pollen from a plant of NUN 51024 CUP. Alternatively, the method comprises growing a plant of NUN 51024 CUP until at least one flower contains pollen and collecting the pollen. In a particular aspect, the pollen is collected when it is mature or ripe. A suitable method for collecting pollen comprises collecting anthers or the part of the anther that contains pollen, for example, by cutting the anther or the part of the anther off. Pollen can be collected in a container. Optionally, collected pollen can be used to pollinate a cucumber flower.

The morphological and/or physiological differences between two different individual plants described herein (e.g., between NUN 51024 CUP and a progeny of NUN 51024 CUP) or between a plant of NUN 51024 CUP or progeny of said variety, or a plant having all, or all but 1, 2, or 3, of the physiological and morphological characteristics of NUN 51024 CUP (or all, or all but 1, 2, or 3 of the characteristics as listed in Table 1) and another known variety can easily be established by growing said variety next to each other or next to the other variety (in the same field, under the same environmental conditions), preferably in several locations which are suitable for said cucumber cultivation, and measuring morphological and/or physiological characteristics of a number of plants (e.g., to calculate an average value and to determine the variation range/uniformity within the variety). For example, trials can be carried out in Acampo Calif., USA (N 38 degrees 07'261"/W 121 degrees 18' 807", USA, whereby various characteristics, for example, maturity, days from seeding to harvest, plant habit, plant attitude, leaf shape, leaf color, blistering, numbers of flowers per leaf axil, number of calyx lobes, number of petals, fruit group, immature fruit color, mature fruit color, pungency, flavor, fruit glossiness, fruit size, fruit shape, average number of fruits per plant, seed size, seed weight, anthocyanin level, disease resistance, insect resistance, can be measured and directly compared for species of cucumber. Thus, the disclosure comprises cucumber plant having one, two or three physiological and/or morphological characteristics which are different from those of the plant of NUN 51024 CUP and which otherwise has all the physiological and morphological characteristics of the plant of NUN 51024 CUP, when determined at the 5% significance level for plants grown under the same environmental conditions. In another aspect, the different characteristic is affected by a mutation, optionally induced mutation, or by transformation.

The morphological and physiological characteristics (and the distinguishing characteristics) of NUN 51024 CUP are provided, for example, in Table 1. Encompassed herein is also a plant obtainable from NUN 51024 CUP (e.g., by selfing and/or crossing and/or backcrossing with said variety and/or progeny of said variety) comprising all or all but one, two or three of the physiological and morphological characteristics of NUN 51024 CUP listed in Table 1 as determined at the 5% significance level for numerical characteristics or identical for non-numerical characteristics when grown under the same environmental conditions and/or comprising one or more (or all; or all except one, two or three) characteristics when grown under the same environmental conditions. The morphological and/or physiological characteristics may vary somewhat with variation in the environment (such as temperature, light intensity, day length, humidity, soil, fertilizer use), which is why a comparison under the same environmental conditions is preferred. Colors can best be measured using the Royal Horticultural Society (RHS) Chart.

Also at-harvest and/or post-harvest characteristics of fruits can be compared, such as cold storage holding quality, post-harvest flesh firmness, and Brix can be measured using known methods. (Fruit) Flesh firmness can for example be measured using a penetrometer, e.g. by inserting a probe into the fruit flesh and determining the insertion force, or by other methods. Fruit flesh firmness can for example be measured using a "FT 327 Penetrometer", available from QA Supplies LLC, 1185 Pineridge Road, Norfolk, Va. 23502.

In yet a further aspect, the disclosure provides for a method of producing a new cucumber plant. The method comprises crossing NUN 51024 CUP, or a plant comprising all but 1, 2, or 3 of the morphological and physiological characteristics of NUN 51024 CUP (as listed in Table 1), or a progeny thereof, either as male or as female parent, with a second cucumber plant (or a wild relative of cucumber) one or more times, and/or selfing a cucumber plant of NUN 51024 CUP, or a progeny plant thereof, one or more times, and selecting progeny from said crossing and/or selfing. The second cucumber plant may, for example, be a line or variety of the species *C. sativus* L., *Cucumis hystrix, Cucumis ritchiei* (syn. *Dicaelospermum ritchiei*) or *Cucumis maderaspatana* (syn. *Mukia maderaspatana*).

The disclosure provides for methods of producing plants which retain all the morphological and physiological characteristics of a plant described herein. The disclosure also provides for methods of producing a plant comprising all but 1, 2, or 3 or more of the morphological and physiological characteristics of NUN 51024 CUP (e.g., as listed in Table 1), but which are still genetically closely related to said variety. The relatedness can, for example be determined by fingerprinting techniques (e.g., making use of isozyme markers and/or molecular markers such as Single-nucleotide polymorphism (SNP) markers, amplified fragment length polymorphism (AFLP) markers, microsatellites, mini satellites, Random Amplified Polymorphic DNA (RAPD) markers, restriction fragment length polymorphism (RFLP) markers and others). A plant is "closely related" to NUN 51024 CUP if its DNA fingerprint is at least 80%, 90%, 95% or 98% identical to the fingerprint of NUN 51024 CUP. In a particular aspect, AFLP markers are used for DNA fingerprinting (Vos et al. 1995, Nucleic Acid Research 23: 4407-4414). A closely related plant may have a Jaccard's Similarity index of at least about 0.8, preferably at least about 0.9, 0.95, 0.98 or more (Parvathaneni et al., J. Crop Sci. Biotech. 2011 (March) 14 (1): 39-43).

The disclosure also provides a plant and a variety obtained or selected by applying these methods on NUN 51024 CUP. Such a plant may be produced by crossing and/or selfing, or alternatively, a plant may simply be identified and selected amongst plants of said variety, or progeny of said variety, e.g. by identifying a variant within NUN 51024 CUP or within progeny of said variety (e.g., produced by selfing) which variant differs from NUN 51024 CUP in one, two or three of the morphological and/or physiological characteristics (e.g., in one, two or three distinguishing characteristics), e.g., those listed in Table 1 or others. In one aspect, the disclosure provides a cucumber plant having a Jaccard's Similarity index with NUN 51024 CUP of at least 0.8, e.g. at least 0.85, 0.9, 0.95, 0.98 or even at least 0.99.

In some aspects, the disclosure provides a cucumber plant comprising genomic DNA having at least 95%, 96%, 97%, 98% or 99% sequence identity compared to the genomic DNA sequence of a plant of NUN 51024 CUP as deposited under Accession Number NCIMB 43122. In some aspects, the cucumber plant further comprises all or all but 1, 2, or 3 of the morphological and physiological characteristics of NUN 51024 CUP (e.g., as listed in Table 1). In other aspects, the cucumber plant is a hybrid or other derived from a seed or plant of NUN 51024 CUP. In other aspects, the cucumber plant comprises the distinguishing characteristics of NUN 51024 CUP.

For the purpose of this disclosure, the "sequence identity" of nucleotide sequences, expressed as a percentage, refers to the number of positions in the two optimally aligned sequences which have identical residues (×100) divided by the number of positions compared. A gap, i.e., a position in the pairwise alignment where a residue is present in one sequence but not in the other, is regarded as a position with non-identical residues. A pairwise global sequence alignment of two nucleotide sequences is found by aligning the two sequences over the entire length according to the Needleman and Wunsch global alignment algorithm described in Needleman and Wunsch, 1970, J. Mol. Biol. 48(3):443-53). A full implementation of the Needleman-Wunsch global alignment algorithm is found in the needle program in The European Molecular Biology Open Software Suite (EMBOSS, Rice et al., Trends in Genetics June 2000, vol. 16, No. 6. pp. 276-277).

The description also provides methods for determining the identity of parental lines of plants described herein, in particular the identity of the female line. WO2013/182646, which is hereby incorporated by reference, relates to a non-destructive method for analyzing maternal DNA of a seed. In this method the DNA is dislodged from the seed coat surface and can be used to collect information on the genome of the maternal parent of the seed. This method for analyzing maternal DNA of a seed comprises contacting a seed with a fluid to dislodge DNA from the seed coat surface, and analyzing the DNA thus dislodged from the seed coat surface using methods known in the art. The skilled person is thus able to determine whether a seed has grown on a plant of a plant of NUN 51024 CUP or is a progeny of said variety, because the seed coat of the seed is a maternal tissue genetically identical to NUN 51024 CUP. In one aspect, the present disclosure relates to a seed coat comprising maternal tissue of NUN 51024 CUP. In another aspect, the disclosure relates to a cucumber seed comprising a maternal tissue of NUN 51024 CUP. In another aspect, the disclosure provides for a method of identifying the female parental line of NUN 51024 CUP by analyzing the seed coat of a seed of that variety, In another aspect, the skilled person can determine whether a seed is grown on NUN 51024 CUP by analyzing the seed coat or another maternal tissue of said seed.

By crossing and/or selfing (one or more) single traits may be introduced into NUN 51024 CUP (e.g., using backcrossing breeding schemes), while retaining the remaining morphological and physiological characteristics of said variety and/or while retaining one or more or all distinguishing characteristics. A single trait converted plant may thereby be produced. For example, disease resistance genes may be introduced, genes responsible for one or more quality traits, yield, etc. Both single genes (e.g., dominant or recessive) and one or more QTLs (quantitative trait loci) may be transferred into NUN 51024 CUP by breeding with said variety.

Alternatively, a single trait converted plant or single locus converted plant of NUN 51024 CUP may be produced by (i) genetically transforming or mutating cells of NUN 51024 CUP; (ii) growing the cells into a plant; and (iii) optionally selecting a plant that contains the desired single locus conversion. The skilled person is familiar with various techniques for genetically transforming a single locus in a plant cell, or mutating said cells.

Any pest or disease resistance genes may be introduced into a plant of NUN 51024 CUP, progeny of said variety or into a plant comprising all but 1, 2, or 3 or more of the morphological and physiological characteristics of NUN 51024 CUP (e.g., as listed in Table 1). Resistance to one or more of the following diseases or pests may be introduced into plants described herein: Angular Leaf Spot (*Pseudomonas lachrymans*), Anthracnose (Race 1), *Colletotrichum lagenaria*, Anthracnose (Race 2), Bacterial Wilt (*Enwinia tracheiphilus*), Cucumber Scab (Gummosis) (*Cladosporium cucumerinum*), Downy Mildew, Powdery Mildew (*Erysiphe chicoracearum*), Alternaria Leaf Blight (*Alternaria cucumerina*), Target Spot (*Corynespora cassiicola*), Cucumber Yellow Mottle Mosaic Virus (*Cucumis* Virus 1), Cucumber Green Mottle Mosaic Virus (*Cucumis* Virus 2), Cucumber *Aucuba* Mosaic Virus (*Cucumis* Virus 2A), Muskmelon Mosaic Virus, Watermelon Mosaic Virus, *Papaya* Ring Spot Virus, Zucchini Mosaic Virus, Cucumber Rust, Root Rot, Crown Blight, Verticillum Wilt, Sulphur Burn, *Fusarium oxysporum* fsp. *cucumberis* (Fom) race 0, *Fusarium oxysporum* fsp. *cucumberis* (Fom) race 1, *Fusarium oxysporum* fsp. *cucumberis* (Fom) race 2, *Fusarium* Wilt R2, Root Knot (Nematode), Anthracnose, and/or Squash Mosaic.

The disclosure also provides a method for developing a cucumber plant in a cucumber breeding program, using a cucumber plant described herein, or its parts as a source of plant breeding material. Suitable plant breeding techniques are recurrent selection, backcrossing, pedigree breeding, mass selection, mutation breeding and/or genetic marker enhanced selection. In one aspect, the method comprises crossing NUN 51024 CUP or progeny of said variety, or a plant comprising all but 1, 2, or 3 or more of the morphological and physiological characteristics of NUN 51024 CUP (e.g., as listed in Table 1), with a different cucumber plant, and wherein one or more offspring of the crossing are subject to one or more plant breeding techniques: recurrent selection, backcrossing, pedigree breeding, mass selection, mutation breeding and genetic marker enhanced selection (see e.g., Martin et al. 2008, Australian Journal of Crop Science 1(2): 43-46). For breeding methods in general see Principles of Plant Genetics and Breeding, 2007, George Acquaah, Blackwell Publishing, ISBN-13: 978-1-4051-3646-4.

The disclosure also provides a cucumber plant comprising at least a first set of the chromosomes of cucumber variety NUN 51024 CUP, a sample of seed of said variety having been deposited under Accession Number NCIMB 43122; optionally further comprising a single locus conversion or a mutation, wherein said plant has essentially all of the morphological and physiological characteristics of the plant comprising at least a first set of the chromosomes of said variety. In another embodiment, this single locus conversion confers a trait: wherein the trait is yield, storage properties, color, male sterility, herbicide tolerance, insect resistance, pest resistance, disease resistance, environmental stress tolerance, modified carbohydrate metabolism or modified protein metabolism.

In one embodiment, a plant of NUN 51024 CUP may also be mutated (e.g., by irradiation, chemical mutagenesis, heat treatment, etc.) and mutated seeds or plants may be selected in order to change one or more characteristics of said variety. Methods such as TILLING may be applied to cucumber populations in order to identify mutants. Similarly, NUN 51024 CUP may be transformed and regenerated, whereby one or more chimeric genes are introduced into the variety or into a plant comprising all but 1, 2, 3, or more of the morphological and physiological characteristics (e.g., as listed in Table 1). Transformation can be carried out using standard methods, such as *Agrobacterium tumefaciens* mediated transformation or biolistics, followed by selection of the transformed cells and regeneration into plants. A desired trait (e.g., gene(s) conferring pest or disease resistance, herbicide, fungicide or insecticide tolerance, etc.) can be introduced into NUN 51024 CUP, or progeny of said variety, by transforming said variety or progeny of said variety with a transgene that confers the desired trait, wherein the transformed plant retains all or all but one, two or three of the phenotypic and/or morphological and/or physiological characteristics of NUN 51024 CUP or the progeny of said variety and contains the desired trait.

The disclosure also provides a plant or a cell of a plant comprising a desired trait produced by mutating a plant of variety NUN 51024 CUP or a cell thereof and selecting a plant the desired trait, wherein the mutated plant retains all or all but one of the phenotypic and morphological characteristics of said variety, optionally as described for each variety in Table 1, and contains the desired trait and wherein a representative sample of seed of variety NUN 51024 CUP has been deposited under Accession Number NCIMB 43122. In a further embodiment, the desired trait is: yield, compact cucumber, fruit quality, male sterility, herbicide tolerance, insect resistance, pest resistance, disease resistance, Powdery mildew resistance without necrosis, environmental stress tolerance, modified carbohydrate metabolism, modified protein metabolism or ripening.

In one aspect, the disclosure provides a method for inducing mutation in NUN 51024 CUP comprising:
 a. exposing a seed, a plant or a plant part or a cell of NUN 51024 CUP to a mutagenic compound or to radiation, wherein a representative sample of seed of NUN 51024 CUP is deposited under Accession Number NCIMB 43122;
 b. selecting a seed, a plant or a plant part or a cell of NUN 51024 CUP having a mutation; and
 c. optionally growing and/or multiplying the seed, plant or plant part or cell of NUN 51024 CUP having the mutation.

The disclosure also provides a plant having one, two or three physiological and/or morphological characteristics which are different from those of NUN 51024 CUP and which otherwise has all the physiological and morphological characteristics of said variety, wherein a representative sample of seed of variety NUN 51024 CUP has been deposited under Accession Number NCIMB 43122. In particular variants which differ from NUN 51024 CUP in none, one, two or three of the characteristics mentioned in Table 1 are encompassed.

A part of NUN 51024 CUP (or of progeny of said variety or of a plant having all physiological and/or morphological characteristics but one, two or three which are different from those of said variety) encompasses any cells, tissues, organs obtainable from the seedlings or plants, such as but not limited to: a cucumber fruit or a part thereof, a cutting, hypocotyl, cotyledon, seed coat, pollen and the like. Such parts can be stored and/or processed further. The disclosure further provides for food or feed products comprising a part of NUN 51024 CUP or a part of progeny of said variety, or a part of a plant having all but one, two or three physiological and/or morphological characteristics of NUN 51024 CUP, comprising one or more of such parts, optionally processed (such as canned, chopped, cooked, roasted, in a sauce, in a sandwich, pasted, puréed or concentrated, juiced, frozen, dried, pickled, or powdered).

In one aspect, the disclosure provides for a haploid plant and/or a doubled haploid plant of NUN 51024 CUP, or of a plant having all but one, two or three physiological and/or morphological characteristics of NUN 51024 CUP, or progeny of any of these, is encompassed herein. Haploid and doubled haploid (DH) plants can, for example, be produced by cell or tissue culture and chromosome doubling agents and regeneration into a whole plant. In a method for DH production chromosome doubling may be induced using known methods, such as colchicine treatment or the like. In one aspect, the method comprises inducing a cell or tissue culture with a chromosome doubling agent, and regenerating the cells or tissues into a whole plant.

In yet another aspect, the disclosure provides for haploid plants and/or doubled haploid plants derived from NUN 51024 CUP that, when combined, make a set of parents of NUN 51024 CUP. The haploid plant and/or the doubled haploid plant of NUN 51024 CUP can be used in a method for generating parental lines of NUN 51024 CUP.

Using methods known in the art such as "reverse synthesis of breeding lines" or "reverse breeding", it is possible to produce parental lines for a hybrid plant such as NUN 51024 CUP. Thus, a skilled person can take any individual heterozygous plant (called a "phenotypically superior plant" in Example 2 of WO2014/076249 hereby incorporated by reference in its entirety; NUN 51024 CUP is such a plant) and generate a combination of parental lines (reverse breeding parental lines) that, when crossed, produce the variety NUN 51024 CUP. It is not necessary that the reverse breeding parental lines are identical to the original parental lines. Such new breeding methods are based on the segregation of individual alleles in the spores produced by a desired plant and/or in the progeny derived from the self-pollination of that desired plant, and on the subsequent identification of suitable progeny plants in one generation, or in a limited number of inbred cycles. Such a method is known from WO2014/076249 or from Wijnker et al., Nature Protocols Volume: 9, Pages: 761-772 (2014) DOI: doi: 10.1038/nprot.2014.049, which are hereby incorporated by reference in their entireties. Thus, the disclosure provides a method for producing parental lines for a hybrid organism (e.g., NUN 51024 CUP), comprising: a) defining a set of genetic markers present in a heterozygous form (H) in a partially heterozygous starting organism; b) producing doubled haploid lines from spores of the starting organism; c) genetically characterizing the doubled haploid lines thus obtained for the said set of genetic markers to determine whether they are present in a first homozygous form (A) or in a second homozygous form (B); and d) selecting at least one pair of doubled haploid lines that have complementary alleles for at least a subset of the genetic markers, wherein each member of the pair is suitable as a parental line for the hybrid organism.

The disclosure also provides a method for producing parental lines for hybrid NUN 51024 CUP comprising: genetically characterizing a doubled haploid line from NUN 51024 CUP to determine whether one or more genetic markers are present in a first homozygous form or in a second homozygous form in said line, wherein the one or more genetic markers are present in a heterozygous form in NUN 51024 CUP; and selecting at least one pair of doubled haploid lines that have complementary alleles for the one or more the genetic markers, wherein each member of the pair is suitable as a parental line for a hybrid organism, optionally this method further comprises defining a set of genetic markers present in a heterozygous form in NUN 51024 CUP; and producing doubled haploid lines from NUN 51024 CUP. Doubled haploid lines generated as described herein can be used in such a method.

Thus, in one aspect, the disclosure relates to a method of producing a combination of parental lines of a plant of NUN 51024 CUP comprising making doubled haploid cells from haploid cells from said plant or a seed of that plant; and optionally crossing these parental lines to produce and collecting seeds. In another aspect, the disclosure relates to a combination of parental lines produced by this method. In still another aspect, the combination of parental lines can be used to produce a seed or plant of NUN 51024 CUP when these parental lines are crossed. In still another aspect, the disclosure relates to a combination of parental lines from which a seed or plant having all physiological and/or morphological characteristics of NUN 51024 CUP (when the characteristics are determined at the 5% significance level for plants grown under the same conditions).

In another aspect, the disclosure comprises a method for making doubled haploid cells from haploid cells of NUN 51024 CUP is comprising doubling cells of NUN 51024 CUP with a doubling agent, such as colchicine treatment (Nikolova and Niemirowicz-Szczytt, (1996) Acta Soc Bot Pol 65:311-317)

In another aspect, the disclosure provides a method of introducing a single locus conversion or single trait conversion or a desired trait into NUN 51024 CUP comprising:
a. obtaining a combination of a parental lines of NUN 51024 CUP, optionally through reverse synthesis of breeding lines,
b. introducing a single locus conversion in at least one of the parents of step a; and
c. crossing the converted parent with the other parent of step a to obtain seed of NUN 51024 CUP A combination of a male and a female parental line of NUN 51024 CUP can be generated by methods described herein, for example, through reverse synthesis of breeding lines.

In another aspect, the disclosure provides a method of introducing a single locus conversion or single trait conversion or a desired trait into NUN 51024 CUP, comprising introducing a single locus conversion in at least one of the parents of NUN 51024 CUP; and crossing the converted parent with the other parent of NUN 51024 CUP to obtain seed of NUN 51024 CUP.

In another aspect, the step of introducing a single locus conversion in at least one of the parents comprises:
i. obtaining a cell or tissue culture of cells of the parental line of NUN 51024 CUP;
ii. genetically transforming or mutating said cells;
iii. growing the cells into a plant; and
iv. optionally selecting plants that contain the single locus conversion, the single trait conversion or the desired trait.

In another method, the step of introducing a single locus conversion in at least one of the parents comprises genetically transforming or mutating cells the parental line of NUN 51024 CUP; growing the cells into a plant; and optionally selecting plants that contain the single locus conversion, the single trait conversion or the desired trait.

In another embodiment, the step of introducing a single locus conversion, single trait, or desired trait in at least one of the parents comprises:
i. crossing the parental line of NUN 51024 CUP with a second cucumber plant comprising the single locus conversion, the single trait conversion or the desired trait;
ii. selecting F1 progeny plants that contain the single locus conversion, the single trait conversion or the desired trait;
iii. crossing said selected progeny plants of step ii with the parental line of step i, to produce a backcross progeny plant;
iv. selecting backcross progeny plants comprising the single locus conversion, the single trait conversion or the desired trait and otherwise all or all but one, two or three of the morphological and physiological characteristics the parental line of step i to produce selected backcross progeny plants; and
v. optionally repeating steps iii and iv one or more times in succession to produce selected second, third or fourth or higher backcross progeny plants comprising the single locus conversion, the single trait conversion or the desired trait and otherwise all or all but one, two or three of the morphological and physiological characteristics the parental line of step i to produce selected backcross progeny plants, when grown in the same environmental conditions.

The disclosure further relates to plants obtained by this method.

In any of the above methods where the single locus conversion concerns a trait, the trait may be yield or pest resistance or disease resistance. In one aspect, the trait is disease resistance and the resistance is conferred to Angular Leaf Spot (*Pseudomonas lachrymans*), Anthracnose (Race 1), *Colletotrichum lagenaria*, Anthracnose (Race 2), Bacterial Wilt (*Erwinia tracheiphilus*), Cucumber Scab (Gummosis) (*Cladosporium cucumerinum*), Downy Mildew, Powdery Mildew (*Erysiphe chicoracearum*), Alternaria Leaf Blight (*Alternaria cucumerina*), Target Spot (*Corynespora cassiicola*), Cucumber Yellow Mottle Mosaic Virus (*Cucumis* Virus 1), Cucumber Green Mottle Mosaic Virus (*Cucumis* Virus 2), Cucumber *Aucuba* Mosaic Virus (*Cucumis* Virus 2A), Muskmelon Mosaic Virus, Watermelon Mosaic Virus, *Papaya* Ring Spot Virus, Zucchini Mosaic Virus, Cucumber Rust, Root Rot, Crown Blight, Verticillum Wilt, Sulphur Burn, *Fusarium oxysporum* fsp. *cucumberis* (Fom) race 0, *Fusarium oxysporum* fsp. *cucumberis* (Fom) race 1, *Fusarium oxysporum* fsp. *cucumberis* (Fom) race 2, *Fusarium* Wilt R2, Root Knot (Nematode), Anthracnose, and Squash Mosaic or Powdery mildew resistance without necrosis.

The disclosure also provides a combination of parental lines which, when crossed, produce a seed or plant having all physiological and/or morphological characteristics of NUN 51024 CUP but one, two or three which are different (when grown under the same environmental conditions), as well as a seed or plant having all physiological and/or morphological characteristics of NUN 51024 CUP but one, two or three which are different (when the characteristics are determined at the 5% significance level for plants grown under the same conditions).

Also provided is a plant part obtainable from variety NUN 51024 CUP or from progeny of said variety or from a plant having all but one, two or three physiological and/or morphological characteristics which are different from those of NUN 51024 CUP, or from a vegetatively propagated plant of NUN 51024 CUP (or from its progeny or from a plant having all or all but one, two or three physiological and/or morphological characteristics which are different from those of NUN 51024 CUP), wherein the plant part is a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed-coat or another maternal tissue which is part of a seed grown on NUN 51024 CUP, or hypocotyl, cotyledon, a scion, a stock, a rootstock, a pistil, an anther, or a flower or a part thereof.

In another aspect, the disclosure provides a method of determining the genotype of a plant described herein comprising detecting in the genome (e.g., a sample of nucleic acids) of the plant at least a first polymorphism or an allele. The skilled person is familiar with many suitable methods of genotyping, detecting a polymorphism or detecting an allele including restriction fragment length polymorphism identification (RFLP) of genomic DNA, random amplified polymorphic detection (RAPD) of genomic DNA, amplified fragment length polymorphism detection (AFLP), polymerase chain reaction (PCR), DNA sequencing, allele specific oligonucleotide (ASO) probes, and hybridization to DNA microarrays or beads. Alternatively, the entire genome could be sequenced. The method may, in certain embodiments, comprise detecting a plurality of polymorphisms in the genome of the plant, for example by obtaining a sample of nucleic acid from a plant and detecting in said nucleic acids a plurality of polymorphisms. The method may further comprise storing the results of the step of detecting the plurality of polymorphisms on a computer readable medium The disclosure also provides for a food or feed product comprising or consisting of a plant part described herein. Preferably, the plant part is a cucumber fruit or part thereof and/or an extract from a fruit or another plant part described herein. The food or feed product may be fresh or processed, e.g., dried, grinded, powdered, pickled, chopped, cooked, roasted, in a sauce, in a sandwich, pasted, puréed or concentrated, juiced, pickled, canned, steamed, boiled, fried, blanched and/or frozen, etc.

Marketable cucumber fruits are generally sorted by size and quality after harvest. Alternatively the cucumber fruits can be sorted by expected shelf life, pH or Brix.

Cucumbers may also be grown for use as rootstocks (stocks) or scions (cions). Typically, different types of cucumbers are grafted to enhance disease resistance, which is usually conferred by the rootstock, while retaining the horticultural qualities usually conferred by the scion. It is not uncommon for grafting to occur between cultivated cucumber varieties and related cucumber species. Methods of grafting and vegetative propagation are well-known in the art.

In another aspect, the disclosure provides to a plant comprising a rootstock or scion of NUN 51024 CUP.

All documents (e.g., patent publications) are herein incorporated by reference in their entirety, including the following cited references:

Acquaah, Principles of Plant Genetics and Breeding, 2007, Blackwell Publishing, ISBN-13: 978-1-4051-3646-4

Colijn-Hooymans (1994), Plant Cell, Tissue and Organ Culture 39: 211-217

Martin et al. 2008, Australian Journal of Crop Science 1(2): 43-46

Nikolova V, Niemirowicz-Szczytt K (1996) Acta Soc Bot Pol 65:311-317
Parvathaneni et al., J. Crop Sci. Biotech. 2011 (March) 14 (1): 39-43.
Pisanu et al. ISHS 2004, Acta Hort. 660
Sang-Gu et al. (1988), Plant Cell, Tissue and Organ Culture 12: 67-74
Sarreb et al. (2002), Plant Cell Tissue, Organ Culture 71: 231-235
Vos et al. 1995, Nucleic Acid Research 23: 4407-4414
Wijnker et al., Nature Protocols Volume: 9, Pages: 761-772 (2014) DOI: 10.1038/nprot.2014.049
U.S. Pat. No. 4,822,949
U.S. Pat. No. 5,349,128
U.S. Pat. No. 5,492,827
U.S. Pat. No. 6,084,152
U.S. Pat. No. 6,765,130
WO2013182646
WO2014076249
WO2016207432
WO2016120438
http://www.ams.usda.gov/AMSv1.0/getfile?dDocName=STELDEV3002687
http://www.ams.usda.gov/AMSv1.0/getfile?dDocName=STELDEV3002687
http://www.upov.int/en/publications/tg-rom/tg061/tg_61_7.pdf

EXAMPLES

Development of NUN 51024 CUP

The hybrid NUN 51024 CUP was developed from a male and female proprietary inbred line of Nunhems. The female and male parents were crossed to produce hybrid (F1) seeds of NUN 51024 CUP. The seeds of NUN 51024 CUP can be grown to produce hybrid plants and parts thereof (e.g., cucumber fruit). The hybrid NUN 51024 CUP can be propagated by seeds or vegetative.

The hybrid variety is uniform and genetically stable. This has been established through evaluation of horticultural characteristics. Several hybrid seed production events resulted in no observable deviation in genetic stability. Coupled with the confirmation of genetic stability of the female and male parents the Applicant has concluded that NUN 51024 CUP is uniform and stable.

DEPOSIT INFORMATION

A total of 2500 seeds of the hybrid variety NUN 51024 CUP have been deposited according to the Budapest Treaty by Nunhems B.V. on Jul. 23, 2018, at the NCIMB Ltd., Ferguson Building, Craibstone Estate, Bucksburn, Aberdeen AB21 9YA, United Kingdom (NCIMB). The deposit will be assigned NCIMB number 43122. A deposit of NUN 51024 CUP and of the male and female parent line is also maintained at Nunhems B.V.

Access to the deposits will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 U.S.C. § 2321 et seq.).

Table 1 shows a comparison between NUN 51024 CUP and its Reference variety based on several trials in various locations. In Table 1, the UPOV characteristics of NUN 51024 CUP and its Reference variety are listed. The most similar variety to NUN 51024 CUP is referred to as Reference Variety, a variety from Nunhems with the commercial name Justina.

TABLE 1

Objective description of NUN 51024 CUP and Reference Variety Justina

| Characteristic | NUN 51024 CUP | Justina |
|---|---|---|
| Cotyledon: bitterness (1 absent/9 present) | 1 | 9 |
| Plant: growth type (1 standard indeterminant/2 standard determinant/3 indeterminant/4 determinant) | 1 | 3 |
| Plant: total length of first 15 internodes (1 very short/3 short/5 medium/7 long/9 very long) | 5 | 3 |
| Plant: Vigor (1 very weak/3 weak/5 medium/7 strong/9 very strong) | 5 | 5 |
| Leaf blade: attitude (1 erect/2 horizontal/3 drooping) | 2 | n.r. |
| Leaf blade: length (3 short/5 medium/7 long) | 5 | 5 |
| Leaf blade: ratio length of terminal lobe/length of blade (1 very small/3 short/5 medium/7 large/9 very large) | 5 | 1 |
| Leaf blade: shape of apex of terminal lobe (1 acute/2 right-angled/3 obtuse/4 rounded) | 3 | n.r. |
| Leaf blade: intensity of green color (3 light/5 medium/7 dark/9 very dark) | 5 | 5 |
| Leaf blade: blistering (1 absent or very weak/3 weak/5 medium/7 strong/9 very strong) | 3 | 3 |
| Leaf blade: undulation of margin (1 absent or very weak/2 moderate/3 strong) | 2 | 2 |
| Leaf blade: dentation of margin (1 very weak/3 weak/5 medium/7 strong/9 very strong) | 3 | n.r. |
| Time of development of female flowers (80% of plants with at least one female flower) (1 very early/3 early/5 medium/7 late/9 very late) | 3 | 5 |
| Plant: sex expression (1 monoecious/2 subgynoecious/3 gynoecious/4 hermaphroditic) | 3 | 3 |
| Plant: number of female flowers per node (1 predominantly one/2 predominantly one or two/3 predominantly two/4 predominantly two or three/5 predominantly three or four/6 predominantly four or five/7 predominantly more than five) | 2 | 4 |
| Ovary: color of vestiture (1 white/2 black) | 1 | 1 |
| Parthenocarpy (1 absent/9 present) | 9 | 9 |
| Fruit: length (1 very short/3 short/5 medium/7 long/9 very long) | 3 | 3 |
| Fruits on main stem (±cm) | 9-12 | n.r. |
| Fruit: diameter (3 small/5 medium/7 large) | 3 | 5 |
| Fruit: ratio length/diameter (1 very small/3 small/5 medium/7 large/9 very large) | 5 | 5 |
| Fruit: core diameter in relation to diameter of fruit (1 very small/3 small/5 medium/7 large/9 very large) | 5 | 5 |

TABLE 1-continued

Objective description of NUN 51024 CUP and Reference Variety Justina

| Characteristic | NUN 51024 CUP | Justina |
|---|---|---|
| Young fruit: shape (1 roundish/ 2 turban-shaped/ 3 egg-shaped/4 inversely egg-shaped/ 5 spindle-shaped/6 oval/7 cylindrical/ 8 elongated-cylindrical/ 9 crescent shaped/10 snake shaped) | 7 | 7 |
| Fruit: shape in transverse section (1 round/ 2 round to angular/3 angular) | 1 | n.r. |
| Fruit: shape of stem end (1 necked/2 acute/3 obtuse) | 3 | 3 |
| Fruit: length of neck (1 very short/ 3 short/5 medium/7 long/9 very long) | 1 | n.r. |
| Fruit: shape of calyx end (1 acute/2 obtuse/ 3 rounded/4 truncate) | 2 | 2 |
| Fruit: shape of calyx end (1 pointed/2 obtuse) | 2 | 2 |
| Fruit: ground color of skin at market stage (1 white/2 yellow/3 green) | 3 | 3 |
| Excluding white varieties: Fruit: intensity of ground color of skin (1 very light/3 light/5 medium/7 dark/ 9 very dark) | 5 | 5 |
| Fruit: ribs (1 absent or weak/2 medium/ 3 strong) | 1 | 1 |
| Fruit: sutures (1 absent/9 present) | 1 | n.r. |
| Fruit : creasing (1 absent/9 present) | 1 | 9 |
| Fruit: degree of creasing (1 very weak/ 3 weak/5 medium/7 strong/9 very strong) | 1 | 3 |
| Fruit: type of vestiture (1 hairs only/2 hairs and prickles/3 prickles only) | 3 | 3 |
| Young fruit: colour of vestiture (1 white/2 black) | 1 | 1 |
| Fruit: density of vestiture (1 very sparse/3 sparse/5 medium/ 7 dense/9 very dense) | 7 | 5 |
| Only varieties with white ovary vestiture: Fruit: color of vestiture (1 white/2 light brown/3 dark brown) | 1 | n.r. |
| Fruit: warts (1 absent/9 present) | 9 | 9 |
| Fruit: size of warts (1 very small/ 3 small/5 medium/7 large/9 very large) | 5 | 5 |
| Fruit: length of stripes (1 absent or very short/3 short/5 medium/ 7 long/9 very long) | 1 | 5 |
| Fruit: dots (1 absent/9 present) | 9 | 9 |
| Fruit: distribution of dots (1 bands only/2 predominantly in bands/ 3 evenly distributed) | 3 | n.r. |
| Fruit: length of fruit containing dots (1 distal 1/3/2 distal 1/2/3 distal 2/3/4 excluding area around peduncle/5 whole length) | 3 | n.r. |
| Fruit: density of dots (1 very sparse/ 3 sparse/5 medium/ 7 dense/9 very dense) | 3 | n.r. |
| Fruit: glaucosity (1 absent or very weak/3 weak/5 medium/ 7 strong/9 very strong) | 1 | n.r. |
| Fruit: length of peduncle (3 short/5 medium/7 long) | 5 | 3 |
| Fruit: ground color of skin at physiological ripeness (1 white/2 yellow/3 green/ 4 orange/5 brown) | 2 | 2 |
| Time of maturity (1 very early/ 3 early/5 medium/ 7 late/9 very late) | 3 | n.r. |

Table 1 contains typical values. Values may vary due to environment. Other values that are substantially equivalent are also within the scope of the disclosure. N.A.=not applicable; n.r.=not recorded.

The invention claimed is:

1. A plant, plant part or seed of cucumber variety NUN 51024 CUP, wherein a representative sample of seed of said variety is deposited under Accession Number NCIMB 43122.

2. The plant part of claim 1, wherein said plant part is a leaf, pollen, an ovule, a fruit, a scion, a root, a rootstock, a cutting, a flower, or a cell.

3. A seed that produces the plant of claim 1.

4. A seed grown on the plant of claim 1, wherein a plant grown from said seed does not differ from the plant of claim 1 when the characteristics are determined at the 5% significance level when grown under the same environmental conditions.

5. A cucumber plant or a part thereof derived from the plant of claim 1 which does not significantly differ from the plant of claim 1 in all of the characteristics of Table 1, when the characteristics are determined at the 5% significance level for plants grown under the same environmental conditions, and wherein a representative sample of seed of cucumber variety NUN 51024 CUP is deposited under Accession Number NCIMB 43122.

6. A cucumber plant or a part thereof derived from the plant of claim 1 which does not differ from the plant of claim 1, when the characteristics are determined at the 5% significance level when grown under the same environmental conditions, wherein a representative sample of seed of cucumber variety NUN 51024 CUP is deposited under Accession Number NCIMB 43122.

7. A tissue or cell culture comprising cells of the plant of claim 1.

8. The tissue or cell culture according to claim 7, comprising cells or protoplasts derived from a plant part suitable for vegetative reproduction.

9. The tissue or cell culture according to claim 7, wherein the plant part is an embryo, a meristem, a cotyledon, a hypocotyl, pollen, a leaf, an anther, a root, a root tip, a pistil, a petiole, a flower, a fruit, a seed, or a stem.

10. A cucumber plant regenerated from the tissue or cell culture of claim 7, wherein the plant has all of the physiological and morphological characteristics of the plant of variety NUN 51024 CUP, when the characteristics are determined at the 5% significance level for plants grown under the same environmental conditions, and wherein a representative sample of seed of cucumber variety NUN 51024 CUP is deposited under Accession Number NCIMB 43122.

11. A method of producing the plant of claim 1, said method comprising vegetatively propagating at least a part of the plant of variety NUN 51024 CUP, wherein a representative sample of seed of said variety is deposited under Accession Number NCIMB 43122.

12. The method of claim 11, wherein the vegetative propagation comprises regenerating a whole plant from said part of the plant of variety NUN 51024 CUP, wherein a representative sample of seed of said variety is deposited under Accession Number NCIMB 43122.

13. The method of claim 11, wherein said part is a cutting, a cell culture or a tissue culture.

14. A vegetative propagated plant of claim 1, or a part thereof, wherein the vegetative propagated plant has all of the physiological and morphological characteristics of the plant of variety NUN 51024 CUP, when the characteristics are determined at the 5% significance level for plants grown under the same environmental conditions, and wherein a representative sample of seed of cucumber variety NUN 51024 CUP is deposited under Accession Number NCIMB 43122.

15. A method of producing a cucumber plant, said method comprising crossing the plant of claim 1 with a second cucumber plant at least once, and selecting a progeny cucumber plant from said crossing and optionally allowing the progeny to form seed.

16. A first generation progeny plant of the plant of claim 1 obtained by selfing or cross-pollinating the plant of claim 1 with another cucumber plant, wherein said progeny plant has all of the physiological and morphological characteristics of cucumber variety NUN 51024 CUP.

17. The first generation progeny plant of claim 16, wherein said progeny plant has all of the physiological and morphological characteristics of the plant of variety NUN 51024 CUP, wherein a representative sample of seed of said variety is deposited under Accession Number NCIMB 43122, when determined at the 5% significance level for plants grown under the same environmental conditions.

18. A cucumber plant derived from the plant of claim 1 having one physiological or morphological characteristic which is different from those of the plant of claim 1 and which otherwise has all the physiological and morphological characteristics of the plant of claim 1, when determined at the 5% significance level for plants grown under the same environmental conditions, wherein a representative sample of seed of cucumber variety NUN 51024 CUP is deposited under Accession Number NCIMB 43122.

19. The plant of claim 1, further comprising a single locus conversion, wherein said plant has otherwise all of the morphological and physiological characteristics of the plant of variety NUN 51024 CUP, wherein a representative sample of seed of said variety is deposited under Accession Number NCIMB 43122, when said characteristics are determined at the 5% significance level for plants grown under the same environmental conditions, optionally wherein the single locus conversion confers male sterility, herbicide tolerance, insect resistance, pest resistance, disease resistance, environmental stress tolerance, modified carbohydrate metabolism, or modified protein metabolism.

20. A method of producing doubled haploids of the plant of claim 1, said method comprising making doubled haploid cell from haploid cells from the plant or seed of cucumber variety NUN 51024 CUP, wherein a representative sample of seed of cucumber variety NUN 51024 CUP is deposited under Accession Number NCIMB 43122.

21. A plant comprising the scion or rootstock of claim 2.

22. A container comprising the plant, plant part, or seed of claim 1.

23. A food, a feed product, or a processed product comprising the plant part of claim 2, wherein the plant part comprises at least a cell of cucumber variety NUN 51024 CUP.

24. A method of producing a cucumber fruit, said method comprising growing the plant of claim 1 until it sets at least one fruit, and collecting the fruit.

25. A method for inducing a mutation in the plant of claim 1, said comprising:
  a. exposing the seed, plant, or plant part of cucumber variety NUN 51024 CUP to a mutagenic compound or to radiation, wherein a representative sample of seed of cucumber variety NUN 51024 CUP is deposited under Accession Number NCIMB 43122; and
  b. selecting the seed, plant, plant part, or cell of cucumber variety NUN 51024 CUP having a mutation.

26. A method for collecting pollen of cucumber variety NUN 51024 CUP, said method comprising growing the plant of claim 1 until at least one flower contains pollen, and collecting the pollen.

27. A method of producing a cucumber plant with a desired trait, said method comprising mutating the plant of cucumber variety NUN 51024 CUP and selecting a mutated plant with a desired trait, wherein the mutated plant otherwise retains all of the physiological and morphological characteristics of the plant of cucumber variety NUN 51024 CUP, when grown under the same environmental conditions, wherein a representative sample of seed of said cucumber variety is deposited under Accession Number NCIMB 43122, and wherein the desired trait is male sterility, herbicide tolerance, insect resistance, pest resistance, disease resistance, environmental stress tolerance, modified carbohydrate metabolism, or modified protein metabolism.

\* \* \* \* \*